United States Patent [19]

Leslie

[11] 4,235,870

[45] Nov. 25, 1980

[54] SLOW RELEASE PHARMACEUTICAL COMPOSITIONS

[75] Inventor: Stewart T. Leslie, Aberdeen, Scotland

[73] Assignee: Syngergistics, New York, N.Y.

[21] Appl. No.: 641,069

[22] Filed: Dec. 15, 1975

Related U.S. Application Data

[60] Division of Ser. No. 476,351, Jun. 5, 1974, Pat. No. 3,965,265, which is a continuation-in-part of Ser. No. 253,746, May 16, 1972, abandoned.

[30] Foreign Application Priority Data

Jun. 3, 1971 [GB] United Kingdom ............... 18839/71

[51] Int. Cl.³ .................... A61K 9/22; A61K 9/26; A61K 9/48
[52] U.S. Cl. .................................. 424/19; 424/22; 424/35; 424/38; 424/362
[58] Field of Search ..................................... 424/14–38

[56] References Cited

U.S. PATENT DOCUMENTS

| | | | |
|---|---|---|---|
| 2,921,883 | 1/1960 | Reese et al. | 424/35 |
| 3,065,143 | 11/1962 | Christenson et al. | 424/35 X |
| 3,079,303 | 2/1963 | Raff et al. | 424/35 X |
| 3,108,046 | 10/1963 | Harbit | 424/38 X |
| 3,133,863 | 5/1964 | Tansey | 424/35 |
| 3,146,167 | 8/1964 | Lantz et al. | 424/19 |
| 3,147,187 | 9/1964 | Playfair | 424/19 |
| 3,266,992 | 8/1966 | De Jong | 424/280 X |

*Primary Examiner*—Shep K. Rose
*Attorney, Agent, or Firm*—Wolder, Gross & Yavner

[57] ABSTRACT

Slow release pharmaceutical compositions comprising a combination of a higher aliphatic alcohol and a hydrated hydroxy-alkyl cellulose in ratio of from 2:1 to 4:1 parts by weight and comprising from 20 to 40 percent by weight of the composition; the method for making the same, and their inclusion in pharmaceutical dosage forms intended for oral administration, to provide a slow release of a therapeutically active compound during a predetermined period of time of from five to ten hours, after oral ingestion by humans and animals.

15 Claims, No Drawings

SLOW RELEASE PHARMACEUTICAL COMPOSITIONS

This is a division of application Ser. No. 476,351, filed June 5, 1974, now U.S. Pat. No. 3,965,256 which is a continuation-in-part application of Applicant's copending patent application, Ser. No. 253,746, filed May 16, 1972.

This invention relates to pharmaceutical compositions providing a controlled slow release of one or more therapeutically active compounds over a predetermined period of time and a method for making the same. It further relates to a combination of a higher aliphatic alcohol and a hydrated hydroxy-alkyl cellulose in ratio of from 2:1 to 4:1 parts by weight and comprising from 20 to 40 percent by weight of the composition, the method for making the same, and their inclusion in pharmaceutical dosage forms intended for oral administration, to provide a slow release of a therapeutically active compound during a predetermined period of time of from five to ten hours, after oral ingestion by humans and animals.

It is known in the pharmaceutical art to prepare pharmaceutical compositions that when administered by the oral route to humans and animals provide for a delayed release of the active ingredient contained in said preparation. The object of such slow release pharmaceutical composition being to delay the release of a medicament from said composition until it has reached a certain portion of the alimentary tract and/or, in addition to provide a controlled release of said medicament over a period of time whereby a desired concentration of the medicament in the blood stream of the human or animal is maintained for a longer period of time than would occur if the medicament was given by conventional medicaments. Slow release formulations are well known to the prior art and include such formulations as enteric-coated pellets, tablets and capsules, and/or pharmaceutical formulations wherein the active ingredients are dispersed in a medium totally insoluble in physiologic fluids or where the release of the active medicament is brought about by a breakdown of the formulation due to a mechanical means.

Thus we find that Lantz, et al., U.S. Pat. No. 3,146,167, patented Aug. 25, 1964, teach a method for the preparation of sustained release pellets that relies upon an anhydrous system including a lipid substance and wicking agent. The essence of the Lantz, et al. invention is to prepare a molten slurry of sustained lipid material incorporating the desired medicament, which is them atomized into a gas medium having a cooling and solidifying effect. In addition to lipid materials forming a sustained release composition, Lantz et al. further teaches the use of a wicking agent to cause a more linear dissolution of medicament. The sustained release lipid material present in the Lantz, et al. process from about 35 percent to about 95 percent by weight, of the weight of the composition and the percentage ratio of sustained release lipid material to wicking agent is from about 35%:1% by weight to 35%:15% by weight at the lower range, to an upper ratio of about 95%:5% by weight of the percentage composition of the weight of total solids present in the composition. The teachings of Lantz, et al. are fundamentally directed toward dry-blend molten compositions which meticulously avoid aqueous or hydrated materials.

Reese, et al., U.S. Pat. No. 2,921,883, patented January, 1960, teaches the use of anhydrous materials and relies on an anhydrous manufacturing process to obtain the slowed release composition comprising a lipid substance and a water soluble cellulose derivative. While Reese, et al., teach the use of a lipid material and water insoluble cellulosic materials, we find Reese, et al. to state that water insoluble cellulose derivatives have particular advantages. (See U.S. Pat. No. 3,921,883, Column 2, lines 32-33). Furthermore, the effective ratio between the lipid material and the cellulosic compound taught by Reese, et al., is from about 1:1 to 9:1. Thus we find that Reese continues to advance the prior art in the use of anhydrous substances to prepare slowed release compositions.

Tansey, in U.S. Pat. No. 3,133,863, patented May 19, 1964 again teaches the use of anhydrous systems to obtain a sustained release therapeutic composition. The basic concept of the Tansey invention involves the preparation of a homogeneous two-face anhydrous medium containing a liquid, a hydrophilic and/or an hydrophobic sol and with or without one or more therapeutic agents present (See Tansey, Column 1, lines 15-18). Throughout the entire Tansey teaching we see a reliance on the use of anhydrous ingredients which gel in the presence of particular organic solvent solutions having various polar ratings. Furthermore, Tansey summarizes the state of the prior art with regard to the use of aqueous media in preparing sustained release tablets as:

"In summary, these techniques are empirical and difficult to manage except possibly to those long experienced in the art."

"It should be further noted that on many occasions the wet granulation method using aqueous menstruums is used where known incompatibilities exist in the presence of moisture. In these formulations, it is necessary to exercise special precautions which may entail vacuum drying and other complicated or relatively expensive procedures."

"Because of the critical nature of both the dry and wet granulaion methods, it is apparent that a more precise technique should be developed." (See Tansey, Column 1, line 72 through Column 2, line 12).

The presence of water is considered to be deleterious to the Tansey process and Tansey now corrects this inherent limitation of the older aqueous tablet systems by providing for cellulose compounds to form gels with anhydrous organic solvent systems all the while taking special care to avoid the use of an hydration step, particularly when a lipid substance is present in a coating composition. Among the cellulose gums capable of forming gels with anhydrous organic solvents are hydroxyethyl cellulose and certain cellulose ethers.

Again, we find a reliance upon an anhydrous system and anhydrous technology to prepare sustained release tablets in order to overcome the inherent limitations of aqueous systems in the preparation of sustained release preparations.

Harbit, U.S. Pat. No. 3,108,046, patented, October, 1963, teaches a method for preparing high dose slow-release tablets to overcome erratic release rates of the tablets prepared according to the then prior art. Harbit teaches the utilization of a lipid waxy material as a delaying substance and includes a binder compound in his tablet formula in accord with the well established practice of the prior art to prepare tablets. It is especially noted that Harbit states that a binder is "not an essential aspect of his invention" (see Harbit, U.S. Pat. No. 3,108,046, Column 4, lines 18-19) and that the cellulose binder substance described by Harbit is not considered by him to be a part of his sustained release system or to contribute any sustained release function in his invention. Thus, we find the prior art to contain many methods for the preparation of sustained or slowed release compositions intended for oral administration of medicaments to humans and animals, and that all of these prior art efforts rely upon essentially anhydrous compositions to overcome the inherent limitations known for the older aqueous preparations. The presence of varying amounts of water has been demonstrated to be the basis for virtually all of the inherent limitations of the conventional sustained acting tablet and capsule dosage forms. This teaching away from the use of aqueous preparations resulted in many different anhydrous formulations, but which have not completely avoided the problems arising for the older preparation. Thus, we find that there is no known reliable method for predicting the release of a medicament over an extended period of time and that a smooth, continuing, uniform release of medicament from an orally administered solid dosage form remains to be accomplished.

It was unexpectedly found that hydrated materials may be utilized to particular advantage in formulating slow release compositions and unexpectedly it was further found that the amount of aforesaid hydrated compound present in such formulation, in particular, the ratio of the weight of hydrated substance to the weight of lipid substance provides a new and unexpected critical control of the rate of release of a medicament incorporated in said hydrated sustained release composition so that an improved slow release pharmaceutical composition is available which permits an accurate prediction of the rate of release of a therapeutically active compound per unit time from a unit dosage-form.

According to the present invention, when a higher aliphatic alcohol is combined with an hydrated hydroxy-alkyl cellulose compound in critical proportions of one to the other, a particularly advantageous composition is formed which delays the release of a therapeutically active compound therefrom. The ratio of the amount of higher aliphatic alcohol to hydrated-alkyl cellulose is critical to controlling the rate of release of the active ingredient in aforesaid formulation and a ratio of higher aliphatic alcohol to hydrated hydroxy-alkyl cellulose of from 2:1 to 4:1, with a prefrred ratio of aforesaid components of 3:1 parts by weight, will result in a slowed uniform release of medicament incorporated in aforesaid composition over a period of at least five hours.

Furthermore, it was unexpectedly found that aforesaid critical ratio of three parts by weight of higher aliphatic alcohol to one part by weight of hydrated hydroxy-alkyl cellulose, results in a new synergistic action which potentiates the rate of drug release for the aliphatic alcohol in the aforesaid combination. When the amount of higher aliphatic alcohol and cellulose derivative, together is 20% by weight of the total weight of the unit dosage form, and the ratio of the aforesaid components being 3:1, then the slow release obtained is the same as if the composition would have contained 45% by weight of said alcohol. Thus, the combination of hydrated hydroxy-alkyl cellulose with higher aliphatic alcohol, wherein the ratio of said higher aliphatic alcohol to hydrated cellulose component is from 2:1 to 4:1, results in a potentiation of the drug release properties of said higher aliphatic alcohol when this compound is used as an agent to achieve a slow release of a selected active ingredient from aforesaid combination.

It was further found that the ratio of the amount of the combined higher aliphatic alcohol and hydrated hydroxy-alkyl cellulose to the weight of the formulation had added special effect in controlling the time period during which the release of the active ingredient from a unit dosage form will occur. Thus, when the aforesaid combination of aliphatic alcohol to hydrated cellulose component is 20% by weight, of the weight of the selected unit dosage form, then the period for the release of active ingredient will be about five hours, but when this concentration of delayed release components is increased to 25% of the weight of the unit dosage form, then the time span of the slowed release of an incorporated medicament will be extended to from six to seven hours, while a unit dosage form containing 30% by weight of the aforesaid combination of higher aliphatic alcohol and hydrated hydroxy-alkyl cellulose will provide a slowed release of active ingredient for a period of from nine to ten hours. The concentration of said slow release composition utilized to prepare the unit dosage form will vary in accord with the selected time period during which the release of the active ingredient is desired. In this manner, sustained release pharmaceutical tablets and capsulses may be prepared to provide a release of the active ingredient over a period of five to ten hours.

In preparing the slow release compositions of the present invention, it is important that the alkyl cellulose component be hydrated. The degree of hydration is critical in that excessive hydration will result in an unmanageable wet granular mass while insufficient hydration of the hydroxy-alkyl cellulose compound will result in an erratic and inferior release rate of medicament from the tablet matrix. The degree of hydration used in practice preferably will be that obtained by the addition of a weight of water of from twice to three times the dry weight of the hydroxy-alkyl cellulose compound utilized. The hydroxy-alkyl cellulose preferred in practice is hydroxyethyl cellulose although the analogous, methyl and propyl cellulose derivatives are satisfactory. The water used in the hydration of the hydroxy-alkyl cellulose compound is added to the dry cellulose powder which is then tumbled or blended to provide a uniform mix. The type of agitation used is of little importance as long as uniform hydration results. The temperature of the water being added is also not critical although the hydration reaction is completed much more rapidly with elevated temperatures and steam vapor may be used effectively to achieve a virtually instantaneous hydration.

The higher aliphatic alcohol that is used in the composition according to the present invention is preferably an alcohol containing from 8 to 18 carbon atoms in chain length and a particularly preferred alcohol is cetyl alcohol. The alcohols described herein may be substituted by a further aliphatic group also containing from 8 to 18 carbon atoms and thus for example cetostearyl alcohol is another alcohol which is preferred according to the invention.

The active therapeutic compound intended for therapy may be incorporated in the higher alcohol before this is blended with the hydrated hydroxy-alkyl cellulose, or it may be incorporated in the hydrated hydroxyalkyl cellulose, before it is incorporated with the higher alcohol or divided among both agents. The active ingredient may be incorporated in the partially, or totally pre-formed blend of the two components, or finally, it may be included with the excipient such as lactose or talc, and incorporated in the blend. Each method of adding the active ingredient has its own particular advantages for use in the manufacture of a particular dosage form.

The desirable advantages of the various steps described above, and the new compositions resulting therefrom are readily demonstrated when we analyze the slow release properties determined for a typical composition of the subject invention, as for example, Formula A, comprising:

Potassium chloride—80 parts by weight
Cetyl alcohol—14 parts by weight
Hydroxyethyl cellulose—4.5 parts by weight
Magnesium stearate—1.5 parts by weight Tablets of the aforesaid composition, (Formula A) were prepared from the dry formulation, that is without prior hydration of the hydroxyethyl cellulose. The procedure used was to dry-blend the potassium chloride with the dry hydroxyethyl cellulose and then incorporating the mixture in the previously molten cetyl alcohol. After cooling, the mass was granulated mechanically; mixed with magnesium stearate and compressed into tablets.

The slow release properties of the tablets were evaluated with the disintegration time test and the dissolution rate test. These tests are well known and well accepted methods for evaluating suitability of tablets for human and animal administration. By determining the rate of release of active medicament from a tablet, (dissolution rate test), the slow release characteristics of a tablet is demonstrated.

The disintegration time test is described by the U.S. Pharmacopeia, XVIII Edition, which sets forth the method, apparatus, and the means for interpreting this test. (See U.S. Pharmacopeia, XVIII Edition, pp. 932–934). This dissolution rate test is also set forth in the U.S. Pharmacopeia as a means to evaluating the availability of active ingredients from a solid dosage form. This test is described in the U.S. Pharmacopeia, XVIII Edition, at pp. 934–935, and is considered to be an objective means of determining the dissolution availability characteristics of a solid dosage form. Since absorption and physiologic availability of a medicament are largely dependent upon having the drug in a dissolved state, suitable dissolution characteristics are an important property of a satisfactory drug product. By determining the dissolution rate for a tablet, the availability of active ingredient released therefrom is readily measured and thereby the suitability of the tablet formula as a slow release tablet dosage form may be evaluated.

The contribution of the higher aliphatic alcohol to the slow release mechanism was evaluated by preparing tablets in accord with Formula A, but eliminating the dry hydroxyethyl cellulose component so that only the cetyl alcohol component remained, (Formula B). Appropriate adjustment in weights of ingredients was made to maintain the same weight ratios of components. The disintegration time and dissolution rate of the tablets were determined (see Table I below).

Tablets were then prepared to contain twice the quantity of cetyl alcohol, and the formula modified accordingly, (Formula C):

Potassium chloride—73 grams
Cetyl alcohol—25 grams
Lubricants—2 grams
Average Tablet Weight—818 mg.

Disintegration time and dissolution rate tests were conducted as noted above, (see Table I below).

Tablets were then prepared utilizing only the dry hydroxyethyl cellulose component, and excluding the cetyl alcohol, so that each tablet contained, (Formula D):

Potassium chloride—90 parts by weight
Hydroxyethyl cellulose—5 parts by weight
Tablet lubricants—5 parts by weight The tablet mixture was dry-blended and compressed into tablets, each weighing 655 mg., and subjected to disintegration time and dissolution rate testing (see Table I below).

Tablets of Formula D were prepared with double the amount of hydroxyethyl cellulose component, (Formula E) and the disintegration time and dissolution rate for these tablets determined, (See Table I below).

TABLE 1

DISINTEGRATION TIME AND DISSOLUTION RATE BEHAVIOR OF DELAYED ACTING FORMULATIONS

| Composition | DISINTEGRATION TIME TEST | TIME | DISSOLUTION RATE TEST[a] Minutes | | | | |
|---|---|---|---|---|---|---|---|
| | | | 15 | 30 | 45 | 60 | 90 |
| Formula A | 20 minutes | | 98%[b] | — | — | — | — |
| Formula B | 90 minutes | | — | 60% | — | 95% | 100% |
| Formula C | 90 minutes | | — | 50% | — | 80% | 100% |
| Formula D | 60 minutes | | 60% | 70% | 80% | 100% | — |
| Formula E | 90 minutes | | 50% | 67% | — | 85% | 100% |

Formula D, but containing hydrated hydroxy alkyl cellulose[c]. The water to cellulose ratio being in parts by weight:

| Ratio (w/w) | | | | | | | |
|---|---|---|---|---|---|---|---|
| 1.5:1 | 40 minutes | | 70% | 85% | 100% | — | — |
| 2.0:1 | 60 minutes | | 70% | — | 100% | — | — |
| 2.5:1 | 60 minutes | | 60% | 82% | 96% | 100% | — |
| 3.0:1 | 90 minutes | | 55% | 80% | — | 93% | 100% |
| 3.5:1 | 120 minutes | | — | — | — | 60% | — |
| 4.0:1 | 120 minutes | | — | — | 60% | — | 88%[d] |

[a]Expressed as the percent of the total weight of active component in the tablet released in the time described.
[b]A dissolution rate of 100% was observed after 20 minutes.
[c]The hydroxyethyl cellulose component of Formula D was hydrated prior to its use in Formula D and utilizing the proportions of water to cellulose set forth. All proportions are stated as parts by weight.
[d]After 120 minutes, the dissolution was 100%.

The effect of hydrating the cellulose component on the disintegration time and dissolution rate of the above formula (Formula D) was conducted utilizing varying ratios of water to cellulose (weight of water:weight of cellulose) of 5.5:1, 2:1, 2.5:1, 3:1, 3.5:1, and 4:1, and the disintegration time and dissolution rate testing repeated (see Table I below).

From the results of the tests described above, it is established that the use of a higher aliphatic alcohol alone or a dry cellulose component alone, does not result in a satisfactory slow release tablet composition. Even when the normally utilized amounts of these agents are doubled, we find no improvement in the slowed release of the active ingredient from the unit dosage form. When the hydroxyethyl cellulose component is utilized as the sole ingredient, neither the hydration of the hydroxyethyl cellulose nor the quantity of hydroxyethyl cellulose in the formula exert a critical effect in delaying the release of medicament from the tablet.

The effect of hydrating the hydroxy-alkyl cellulose component of Formula A was evaluated. Tablets of Formula A were prepared, but the hydroxyethyl cellulose component was now hydrated with water prior to its incorporation into the formulation. In order to demonstrate the criticality of the quantity of water utilized to hydrate the cellulose component, varying ratios of weight of water to weight of cellulose component were utilized which these ranged from 1:1 to 6:1, and in particular included the following ratios: 1:1, 2:1, 3:1, 3.5:1, 4:1, and 6:1. The effect of hydration on the tablet composition was then analyzed with the disintegration time test and dissolution rate test and the results reported in Table II below. It is readily apparent from the results described in Table II that hydration of the cellulose component prior to incorporation into the basic sustained release formulation is critical and essential. Furthermore, the range in hydration of said hydroxy alkyl cellulose component is to be critically controlled to be within the range of the ratio of from two parts of water for each part of cellulose component, to four parts of water to each part of cellulose component, all parts being by weight. When the ratio of water to cellulose component falls below 2:1 then insufficient hydration occurs and erratic release patterns result, and when the amount of water is greater than that of 4:1 then the mass is too wet and is not suitable to tablet compression.

the present sustained slow release composition, are not critical to the present invention. Examples of such pharmacologically active ingredients are nitroglycerin and other nitrate compounds, vasodilators, salicylate and acetyl-salicylate compounds, antibiotic substances, sulfonamide drugs; anti-cholinergic compounds, sedatives, tranquillizing and hypnotic agents, psychotropic mood elevating medicaments, anti-inflammatory steroid compounds, broncho-dilating agents, cardiotonic agents, cardio-antiarrhythmic agents, water-soluble ionic metabolites and vitamines. Other medicaments requiring frequency repeated dosage administration by the oral route to maintain a therapeutically active blood level are particularly suitable for inclusion into the present slow release composition. Thus it will be seen that the scope of utility of the aforesaid slow release compositions are not limited to one particular active ingredient neither is the slowed release action achieved with only one class of active therapeutic compound, but arises from the properties of the new pharmaceutical composition formed.

The preferred unit dosage forms for the administration of sustained release medication are tablets and capsules. When it is desired to prepare tablets containing the slow release composition, then it is preferred to utilize an inert diluent such as lactose or talc, to achieve the appropriate concentration of slow release composition within said unit dosage form. Such other ingredients as tablet binders, granulating aides, colors and flavoring materials as are well known to the tableting art may also be included in the finished formulation. A granulation mixture is prepared and compressed into tablets of suitable size and shape, containing the desired quantity of sustained slow release composition to achieve a slow release of the active ingredient over a predetermined time period.

It was further unexpectedly found that the same controlling ratio of parts by weight of water to parts by weight of cellulose component or from 2:1 to 4:1, was a critical ratio of the proportion of selected higher aliphatic alcohol to cellulose component in the formula. Thus, it was determined that for optimal tablet compression requirements and for uniform rate of dissolution of active medicament, a preferred range of higher fatty alcohol to hydrated cellulose component is between 2 parts by weight fatty alcohol for each part of hydrated cellulose component, up to 4 parts by weight

TABLE II

THE ROLE OF HYDRATION OF THE CELLULOSE COMPONENT OF A SLOW RELEASE COMPOSITION ON DISINTEGRATION TIME AND DISSOLUTION RATE OF ACTIVE MEDICAMENT

FORMULA A TABLETS

| HYDRATION RATIO WATER:CELLULOSE | DISINTEGRATION TIME Minutes | DISSOLUTION RATE[a] Minutes | | | | | | |
|---|---|---|---|---|---|---|---|---|
| | | 30 | 60 | 120 | 180 | 240 | 300 | 360 |
| 1:1 | 80–120 | 70% | 90% | 100% | —% | —% | —% | —% |
| 2:1 | 120–240[a] | 16 | 28 | 74 | 81 | 100 | — | — |
| 3:1 | 300 | — | 7 | 26 | 48 | 72 | 100 | — |
| 3.5:1 | 360 | — | 9 | 24 | 43 | 67 | 91 | 100 |
| 4:1 | 360 | — | 7 | 26 | 41 | 62 | 87 | 100 |
| 6:1 | Tablet mass not compressable | | | | | | | |

[a]Values reported are cumulative percentile fractions.

Thus, the critical and essential range of hydration of the cellulose component is from 2 parts of water for each part of cellulose component to 4 parts for each part of cellulose, with a preferred hydration ratio being 3:1.

Both the pharmacologic nature of the active therapeutic ingredient and the dosage to be incorporated into of faty alcohol for each part of hydrated cellulose component. When lesser proportions of fatty alcohol to cellulose components are utilized then an uneven release of active medicament occurs, and when greater concentration of fatty alcohol are used then a more brittle tablet results which does not release material over the desired time span. Moreover, it was determined that the aforesaid range in proportion of fatty alcohol to hydrated cellulose component of from 2:1 to 4:1, also acts to increase the drug release potential of the fatty alcohol so that a lesser quantity of fatty alcohol may be utilized in the formulation thereby affecting a more pharmaceutically elegant tablet and uniform disintegration time.

Slow release capsules may be prepared by filling the appropriate quantity of the above described tablet granulation mixture into gelatin capsules of suitable size and shape. Such modification of the tablet formulation as deemed necessary as for example the elimination of the tablet lubricant or the tablet binder, may be accomplished without effecting the slow release properties of the resultant capsule. Moreover, the preparation of a tablet granulation mix may not be required, in certain circumstances, to prepare slow release capsules. Thus, a slow release capsule may contain the mixture of the appropriate quantity of the combination of higher aliphatic alcohol and hydrated hydroxy-alkyl cellulose, as herein described, together with an active ingredient and diluent. The diluent is necessary to achieve the appropriate concentration of the slow release composition within the unit dosage form. As for the slow release tablet preparations, the time span for the release of the active ingredient in the capsule formulation will depend upon the concentration of the slow release composition within the total weight of the capsule formulation. Thus, when the capsule formulation contains 20% by weight of the new slow release composition, then the active ingredient will be released over a period of five hours, but when this concentration is increased to 25% by weight, the span of release of the active ingredient is increased to 6 to 7 hours and when the concentration of the slow release composition is 30% by weight of the formulation, then the span time for the release of the active ingredient will be 9 to 10 hours.

When it is desired to utilize the aforesaid slow release composition in therapy in the dosage form of sustained slow release tablets or capsules, then the frequency of unit dosage administration will vary with the properties of the active ingredient selected as well as the individual patient's requirements. Thus, a compound intended to provide a slow release of a hypnotic agent will preferably be administered once, at bedtime, whereas a psychotropic mood elevating compound will be administered upon arising. A compound intended to produce bronchodilation or peripheral vasodilation may be administered at suitable intervals throughout the day.

In a similar manner, the duration of the slow release period selected will depend upon the nature of the active ingredient used and the entity being treated. A preparation intended to be administered during the waking hours will commonly have two doses spaced at 5 hour intervals whereas a preparation intended to be used for sustained 24 hour therapy may have 3 doses spaced about 8 hours apart. In practice, the particular therapeutic requirements will determine the selected proportion to be used.

A special advantage of the present sustained acting medication is that it now permits the administration of medicinals to animals during veterinary medical practice. Here the problems of administering a solid dosage form are such as to make the procedure most difficult and therefore, short-acting solid medications which require frequent multiple administrations are avoided. The use of the above described sustained acting dosage forms results in an improved therapeutic armamentorium in the treatment of veterinary disease.

The following examples illustrate the invention but it is not intended to be limited thereby.

EXAMPLE 1

In a suitable vessel, one part by weight of hydroxy ethyl cellulose is hydrated with three parts by weight of water. The mixture is stirred until a granular paste is formed. In another vessel, three parts by weight of cetyl alcohol are melted and to it are added nine parts by weight of a diluent, such as lactose or talc. The whole is granulated through a No. 16 standard mesh stainless steel screen.

The granules of cetyl alcohol are added to the hydrated hydroxy ethyl cellulose in concentration ratio by weight of three parts of cetyl alcohol to one part hydroxy ethyl cellulose. The whole is then well blended and to it is added the selected active ingredient as well as further diluents to achieve the appropriate weight composition of the formulation to permit compression into tablets of suitable size and shape thereby permitting a slow release of active ingredient after the tablets have been administered to a human or animal.

If it is desired to utilize a capsule unit dosage form, then the aforesaid granulation mix which was obtained prior to the tableting step, is filled into capsules of suitable size and shape.

If a sustained release of active ingredient from either the tablet or capsule is desired to be over a period of five hours, then sufficient diluent should be added so that the total amount of combined cetyl alcohol-hydrated hydroxy ethyl cellulose components is 20 percent by weight of the unit weight of the tablet or capsule formulation, but if the release of active ingredient is desired to be over a period of six to seven hours, then the aforesaid combination of cetyl alcohol and hydrated hydroxy ethyl cellulose should constitute 25 percent by weight of the weight of the unit dose and if the release of active ingredient from the tablet is desired to be for a period of nine to ten hours, then the aforesaid combined cetyl alcohol-hydrated hydroxy ethyl cellulose components should constitute 30 percent by weight of the respective formulation.

EXAMPLE 2

When it is desired to prepare a tablet containing nitroglycerin, as an active ingredient to be used in the prophylactic treatment against angina pectoris, the following formulation will be found desirable:

Cetyl Alcohol—15.0% w/w
Hydroxy Ethyl Cellulose—5.0% w/w
Lactose—45.5% w/w
Talc—15.0% w/w
Nitroglycerin 1:10—16.0% w/w
Talc and Magnesium Stearate q.s.—100.0% w/w The nitroglycerin tablet is manufactured as follows:

Step 1: Melt the cetyl alcohol in a water jacketed tank fitted with a stirrer; add the lactose and blend. Granulate the free flowing mass through a No. 16 stainless steel screen.

Step 2: Hydrate the hydroxy ethyl cellulose with three volumes of water for each part by weight of hydroxy ethyl cellulose, and stir until a granular paste is obtained.

Step 3: Add the granules from Step 1 to the paste obtained from Step 2. Continue the blend and add the talc and nitroglycerin powder. Blend until a uniform granular mass is obtained.

Step 4: The granules are then dried at 45° C. for 30 minutes and after drying, granulated through a No. 16 standard mesh screen.

Step 5: The tablet lubricants (magnesium stearate and talc) are then added in suitable quantity and the mixture compressed into tablets.

Compression Data:
Tablet Weight is 400 mg.
Punch size: 3/8 inch; Flat Bevelled Edge.

Tablets prepared in the above described manner, when tested in vitro, present the following slow release rate of nitroglycerin.

| After: | Release of Nitroglycerin (Percentage by Weight) |
| --- | --- |
| 1 hour in artificial gastric media | 8% |
| 2 hours in artificial pancreatic media | 17% |
| 3 hours in artificial pancreatic media | 20% |
| 4 hours in artificial pancreatic media | 30% |
| 5 hours in artificial pancreatic media | 25% |
| Total | 100% |

The concentration of cetyl alcohol and cellulose component in the above described tablet formulation, is 20 percent by weight of the weight of the formulation. By increasing aforesaid concentration of alcohol and cellulose derivative so that it is 25 percent by weight of the tablet formulation, then the release of the nitroglycerin from said tablet will extend over a period of six to seven hours and by increasing the aforesaid concentration of alcohol and cellulose derivative in the formulation to be 30 percent by weight, the release of nitroglycerin from the tablet will extend over a period of nine to ten hours.

EXAMPLE 3

Cetyl Alcohol—18.75% w/w
Lactose—40.50% w/w
Hydroxyl Ethyl Cellulose—6.25% w/w
Talc—15.00% w/w
Nitroglycerin 1:10—16.00% w/w
Tablet Lubricants, q.s.—100.00% w/w Method of Manufacture: The procedure described in Examples 1 and 2 are followed to produce a tablet granulation mix which is then compressed into tablets of suitable size and shape. The release of nitroglycerin from said tablet will occur over a period of from six to seven hours. If the above described formulation is filled into gelatin capsules of suitable size and shape, then a similar slow sustained release of nitroglycerin from the ingested capsule will be observed.

By appropriate adjustment of the concentration of the blend of cetyl alcohol and hydrated hydroxy ethyl cellulose so that the combined weight is 30 percent of the total formula weight, then the release of nitroglycerin will be about nine to ten hours.

EXAMPLE 4

Cetyl Alcohol—20.00% w/w
Aminophylline—73.00% w/w
Hydroxy Ethyl Cellulose—5.00% w/w
Tablet Lubricants, q.s.—100.00% w/w Manufacturing Procedure:
Step 1: Melt the cetyl alcohol in a water jacketed tank. Hold the cetyl alcohol melt at 60°–70° C. and incorporate with stirring the aminophylline. Granulate the resultant mass through a No. 16 standard mesh sieve. Harden the granules by drying at room temperature.

Step 2: Hydrate the hydroxy ethyl cellulose in a suitable vessel fitted with a mixer using two and one-half volumes of water for each part by weight of hydroxy ethyl cellulose.

Step 3: Incorporate the blend from Step 1. Total blending time three hours.

Step 4: Dry the resultant granular mass from Step 3 at 40° C. and pass through a No. 16 standard mesh sieve.

Step 5: Add tablet lubricant and compress into tablets of suitable size and shape or fill into appropriate gelatin capsules.

EXAMPLE 5

Cetyl Alcohol—14.00 gms.
Potassium Chloride—82.00 gms.
Hydroxy Ethyl Cellulose—4.50 gms.
Talc—1.50 gms.

Manufacturing Procedure:
Step 1: To 10 gms. of water at 50° C., contained in a suitable vessel, fitted with a stirrer, add the hydroxy ethyl cellulose. Blend until a uniformly hydrated granular mass is formed.

Step 2: Add to the hydrated cellulose granules, with constant stirring, the potassium chloride. Continue mixing until a free-flowing uniform granule blend is obtained.

Step 3: Dry the cellulose-potassium chloride granules for 30 minutes at 50° C. Granulate the dried granules through a No. 16 stainless steel standard mesh screen.

Step 4: Melt the cetyl alcohol in a water jacketed tank fitted with an efficient stirrer. Hold the melt at 50°–60° C. and incorporate the granules from Step 3. Continue stirring until a free-flowing granular mass is obtained. Allow the mass to cool and granulate through a No. 16 standard mesh stainless steel screen.

Step 5: Lubricate the granules with talc and compress into cores.

Core Compression Data

Core Weight—750.0 mg.
Punch Size—7/16th inch. Deep Concave

Step 6: The cores are then pan-coated using normal coating techniques.

EXAMPLE 6

Cetyl Alcohol—10 gm.
Hydroxy Ethyl Cellulose—5 gm.
Papaverine Hydrochloride—75 gm.
Talc—10 gm.

Manufacturing Procedure:
Step 1: Melt the cetyl alcohol in a jacketed vessel and incorporate the papaverine hydrochloride, blend well and granulate through a No. 16 standard mesh sieve. Dry at room temperature.

Step 2: Hydrate the hydroxy ethyl cellulose with 15 gm. of water.

Step 3: Blend the granules obtained as a result of Step 1 with the hydrated cellulose component of Step 2 and mix well.

Step 4: Granulate the whole through a No. 16 standard mesh sieve and dry.

Step 5: Compress into tablets of suitable size and shape.

EXAMPLE 7

When it is desired to incorporate a pharmacologically active compound with the slow release composition of Example 1 above, then said active agent may be added to the alcohol component or the cellulose component or divided between the two. The incorporation of pharmacologically active agent may also be accomplished after the slow release composition has been formed.

The particular method used to incorporate said active agent will depend on the nature of the compound and the size of the batch being manufactured. The amount of said active ingredient to be incorporated will depend on the therapeutic response desired and also on the excretion pattern of the selected compound. A compound which is rapidly excreted will require a greater amount to be included in a unit dosage form than a compound that is slowly excreted. These factors, however, will also influence the dosage spacing of the daily regimens.

The following examples of pharmacologically active compounds are particularly suitable for administration to human and animals in the form of slow release medications:

nitroglycerin and other nitrate compounds, vasodilators, salicylate and acetyl-salicylate compounds, antibiotic substances, sulfonamide drugs, anticholinergic compounds, sedatives, tranquilizing and hypnotic agents, psychotropic mood elevating medicaments, anti-inflammatory steriod compounds, broncho-dilating agents, cardiotonic agents, cardio-antiarrhythmic agents, water-soluble ionic metabolites and vitamins.

Examples of particular pharmacologically active compounds and their concentration range per unit dosage form are as follows:

| Active Ingredient | Range in Concentration Dosage Per Tablet/Capsule | |
|---|---|---|
| Aspirin | 5–10 | grains |
| Meglumine Salicylate | 5–10 | grains |
| Quinidine Sulfate | 3–5 | grains |
| Quinidine Hydrochloride | 3–5 | grains |
| Quinidine Polygalacturonate | 3–5 | grains |
| Cortisone | 1–5 | mg. |
| Cortisone Acetate | 1–5 | mg. |
| Prednisolone | 1–5 | mg. |
| Sodium Penicillin | 100–500 | mg. |
| Potassium Penicillin | 100–500 | mg. |
| Erythromycin | 100–500 | mg. |
| Thorazine | 10–50 | mg. |

To prepare the appropriate slow release unit dosage form containing the above described pharmacologically active ingredient, any member of the classes of therapeutically active compounds and the particular pharmacologically active compound set forth above may be blended with an appropriate quantity of the composition of claim 1. To this mixture is added an appropriate quantity of diluent to provide the predetermined concentration of from 20 percent to 30 percent by weight of the weight of the slow release composition in order to provide the desired time span for the release of the active ingredient. Such diluents as talc and lactose may be used. The manufacturing procedures described in Examples 1 through 6 may be utilized.

EXAMPLE 8

When it is desired to treat a patient presenting the symtoms of angina pectoris, then the slow release composition obtained as a result of Examples 2,3,6 and 7 are administered orally two to three times daily depending upon the severity of the disease.

When it is desired to obtain a broncho-dilation in humans and animals, then the slow release preparation obtained as a result of Examples 4, and 7 is administered orally two to three times daily.

When it is desired to provide potassium ion supplementation to humans or animals, then the slow release preparation obtained as a result of Examples 5 and 7 is administered two to three times daily.

EXAMPLE 9

In place of the cetyl alcohol used as described in Examples 1 through 7, there may be substituted in an equivalent amount, any one of the higher aliphatic alcohols having from 8 to 18 carbon atoms in chain length and mixtures of these. Such higher aliphatic alcohols as ceto-stearyl alcohol may be substituted in equal quantities for the cetyl alcohol described above. Of the group of higher aliphatic alcohols, lauryl alcohol, myristyl alcohol and stearyl alcohol will be found to be particularly desirable alternate alcohols for the cetyl alcohol described above.

In place of the hydroxy ethyl cellulose described above, there may be substituted in equal quantities, hydroxy methyl cellulose, hydroxy propyl cellulose and mixtures of these.

When the above described alternate components are used, the ratio of higher aliphatic alcohol to hydroxy alkyl cellulose remains between 2:1 and 4:1, with the optimal ratio of 3:1 parts by weight. The remainder of the manufacturing steps are identical to that described for the preparations containing cetyl alcohol and hydroxy ethyl cellulose in Examples 1 through 7 above.

What is claimed is:

1. A composition for use in admixture with pharmacologically active compounds to sustain release thereof over a prolonged period after oral ingestion, the composition comprising a higher aliphatic alcohol selected from the group consisting of aliphatic alcohols with the formula ROH, wherein R is an alkyl group having from 8 to 18 carbon atoms in chain length, ceto-stearyl alcohol and mixtures thereof, admixed with a hydrated hydroxy alkyl cellulose compound selected from the group consisting of hydroxymethyl cellulose, hydroxyethyl cellulose, hydropropyl cellulose and mixtures thereof, the cellulose compound having been hydrated with from 2 to 4 parts by weight water per part of dry hydroxyalkyl cellulose compound prior to admixture, the weight ratio of said aliphatic alcohol to said cellulose compound being within the range of from 2:1 to 4:1.

2. The slow release pharmaceutical composition of claim 1 said alcohol component being selected from the group consisting of lauryl alcohol, myristyl alcohol, stearyl alcohol and mixtures of the same.

3. The slow release pharmaceutical composition of claim 1, said alcohol being cetyl alcohol and said cellulose compound being hydrated hydroxy ethyl cellulose, said proportion of cetyl alcohol to hydrated hydroxy ethyl cellulose compound being 3:1 parts by weight.

4. A method for the preparation of a slow-release pharmaceutical preparation, the composition comprising a higher aliphatic alcohol and a hydrated hydroxyalkyl cellulose compound, the process comprising:

(a) melting and granulating a higher aliphatic alcohol having the formula ROH, wherein R is selected from the group consisting of alkyl groups having from 8 to 18 carbon atoms in chain length and ceto-stearyl alcohol and mixtures thereof, (b) hydrating a hydroxyalkyl cellulose selected from the group consisting of hydroxymethyl cellulose, hydroxyethyl cellulose, hydroxypropyl cellulose and mixtures thereof, the cellulose compound being hydrated with 2 to 4 parts of water for each part by weight of dry cellulose compound and granulating said hydrated cellulose compound, (c) blending the granulated cellulose compound with the granulated alcohol, and (d) drying the blend to obtain a composition capable of providing a sustained, or slow, release of a pharmacologically active material.

5. A pharmaceutical capsule for providing the slow release of a therapeutic agent, the capsule comprising a therapeutically sufficient quantity of a pharmacologically active compound in admixture with a slow-release composition comprising a higher aliphatic alcohol selected from the group consisting of aliphatic alcohols with the formula ROH, wherein R is an alkyl group having from 8 to 18 carbon atoms in chain length, ceto-stearyl alcohol and mixtures thereof, admixed with a hydrated hydroxyalkyl cellulose compound selected from the group consisting of hydroxymethyl cellulose, hydroxyethyl cellulose, hydroxypropyl cellulose and mixtures thereof, the cellulose compound having been hydrated with from 2 to 4 parts by weight water per part of dry hydroxyalkyl cellulose compound prior to admixture, the weight ratio of said aliphatic alcohol to said hydrated cellulose compound being within the range of from 2:1::4:1, and a diluent, the proportion of said slow-release composition in the capsule being in the range of from 20% to 30% by weight of the total weight of the capsule.

6. The capsule of claim 5, said pharmacologically active compound being nitroglycerin.

7. The capsule of claim 5, said pharmacologically active compound being potassium hydrochloride.

8. The capsule of claim 5, said pharmacologically active compound being papaverine hydrochloride.

9. The capsule of claim 5, said pharmacologically active compound being aminophylline.

10. A method for achieving a delayed release and sustained availability of a pharmacologically active substance over a period of from 5 to 10 hours after ingestion, the process comprising the steps of orally administering to a human or animal a slow-release pharmaceutical composition comprising a higher aliphatic alcohol selected from the group consisting of aliphatic alcohols with the formula ROH, wherein R is an alkyl group having from 8 to 18 carbon atoms in chain length, ceto-stearyl alcohol and mixtures thereof, admixed with a hydrated hydroxyalkyl cellulose compound selected from the group consisting of hydroxymethyl cellulose, hydroxyethyl cellulose, hydroxypropyl cellulose and mixtures thereof, the cellulose compound having been hydrated with from 2 to 4 parts by weight water per part of dry hydroxyalkyl cellulose compound, prior to admixture the weight ratio of said aliphatic alcohol to said hydrated cellulose compound being within the range of from 2:1::4:1.

11. The method of claim 10, wherein the pharmaceutical composition is in the form of a tablet.

12. The method of claim 10, wherein the pharmaceutical composition is administered within a gelatin capsule.

13. In a process for providing a sustained release pharmaceutical composition comprising admixing an aliphatic alcohol having the formula ROH wherein R comprises an alkyl group having from 8 to 18 carbon atoms in chain length, ceto-stearyl alcohol and mixtures thereof, with a pharmacologically-active compound, the improvement which comprises preliminarily admixing the aliphatic alcohol with a hydrated hydroxyalkyl cellulose compound, the cellulose compound having been hydrated with from two to four parts by weight of water per part of dry cellulose compound so as to form a uniform blend therewith.

14. The process of claim 13, comprising in addition admixing a diluent therewith.

15. The process of claim 14, comprising in addition drying the uniform blend.

* * * * *